United States Patent [19]

Sekihara et al.

[11] Patent Number: 5,426,365
[45] Date of Patent: Jun. 20, 1995

[54] METHOD AND SYSTEM FOR DETERMINING ELECTROMOTIVE FORCE OR IMPRESSED CURRENT DISTRIBUTION IN AN OBJECT BASED ON MAGNETIC FIELD DISTRIBUTION MEASURED OUTSIDE THE OBJECT

[75] Inventors: Kensuke Sekihara, Musashimurayama; Yukiko Ogura, Kokubunji, both of Japan

[73] Assignee: Hitachi, Ltd., Tokyo, Japan

[21] Appl. No.: 13,425

[22] Filed: Feb. 4, 1993

[30] Foreign Application Priority Data

Feb. 12, 1992 [JP] Japan .................................. 4-025007

[51] Int. Cl.$^6$ .......................... G01R 33/02; A61B 5/05
[52] U.S. Cl. ................................ 324/260; 128/653.1; 128/731; 128/734; 364/413.02
[58] Field of Search .......... 324/244, 248, 260; 128/653.1, 734, 653.2, 731, 732; 364/413.01, 413.02, 480–484

[56] References Cited

U.S. PATENT DOCUMENTS

| | | | |
|---|---|---|---|
| 4,263,920 | 4/1981 | Tasto et al. | 128/734 |
| 4,486,835 | 12/1984 | Bai et al. | 364/414 |
| 5,170,119 | 12/1992 | Sekihara et al. | 324/260 |
| 5,243,984 | 9/1993 | Ogura et al. | 364/413.02 X |

FOREIGN PATENT DOCUMENTS 3202720  9/1991  Japan .

OTHER PUBLICATIONS

Digital Image Restoration, 1977, (Pub.) pp. 148–149, Prentice-Hall, Inc.
Influence of volume currents to neuromagnetic images SPIE, Proceedings, vol. 1351, pp. 399–409, Jul. 1990.
Linear Estimation Approach to Biomagnetic Imaging 1989 (Pub.), pp. 603–606.
An Evaluation of Methods for Neu. Image, IEEE trans., Sep. 1987, pp. 713–723.
Linear Estimation Theory, Applied Optics, vol. 29, No. 5 Feb. 1990 pp. 658–667.
Journal of Magnetism and Magnetic Material, Biomagnetism, by S. J. Williamson and L. Kaufman, pp. 129-150-151, 1981.
Phys. Med. Biol., Basic mathematical and electromagnetic concepts of the biomagnetic inverse problem, 1987, vol. 32, No. 1, pp. 11–12.

Primary Examiner—Sandra L. O'Shea
Assistant Examiner—Jay M. Patidar
Attorney, Agent, or Firm—Antonelli, Terry, Stout & Kraus

[57] ABSTRACT

In a magnetic field generation source measuring method and system for determining a magnetic field generation source in an object to be examined from a magnetic field in the interior of the object measured at the exterior of the object, the object is represented by a model in which the object is divided into a plurality of cells. The resistance values of each cell in x, y and z directions are determined from information concerning the electric conductivity of the interior of the object beforehand measured. Supposing the distribution of electromotive forces in the object as a current source, a return current generated in accordance with the electromotive force distribution in the object is determined by use of estimated values of the intensities of the current source in the x, y and z directions and the resistance values. A vector of the sum of a current of the current source and the return current is determined for all of the cells. The second power of the absolute value of a difference between the vector of the sum and a current vector determined from the magnetic field in the interior of the object measured at the exterior of the object is subjected to summation for all of the cells. The estimated values of the current source intensities, which minimize the summation, are determined as an electromotive force distribution in the object.

6 Claims, 3 Drawing Sheets

METHOD AND SYSTEM FOR DETERMINING ELECTROMOTIVE FORCE OR IMPRESSED CURRENT DISTRIBUTION IN AN OBJECT BASED ON MAGNETIC FIELD DISTRIBUTION MEASURED OUTSIDE THE OBJECT

BACKGROUND OF THE INVENTION

The present invention relates to a magnetic field source measuring method and system in which a magnetic field distribution on an external surface of an object such as a living body to be examined is measured to determine the distribution of magnetic field generation sources in the interior of the object from data of the measured magnetic field distribution and the determined magnetic field generation source distribution is displayed.

There are known techniques for determining a current distribution in an object such as a living body from a magnetic field distribution on an external surface of the object. Since the current distribution in the object and the magnetic field distribution on the surface of the object are related with each other by the Biot-Savart's equation, the current distribution in the object can be determined by measuring the magnetic field distribution on the object surface and discretely performing an inverse operation of the Biot-Savart's equation.

The current distribution thus determined includes an impressed current in which an electromotive force attendant upon the activity of the living body is directly reflected and a return current which is subsidiarily generated from the impressed current. Accordingly, in order to accurately visualize the activity of the living body, it is necessary to remove a return current component from a current distribution which is obtained from the inverse operation of the Biot-Savart's equation (hereinafter referred to as total current distribution).

One example of a method of removing the return current component has been proposed by, for example, W. H. Kullmann, SPIE Proceedings, Vol. 1351, pp. 399-409. According to the proposed method, when the distribution S of electric conductivities in a living body is uniform, the following expression is satisfied owing to the continuity of current:

$$S\nabla^2 V = -\nabla \cdot P \quad (1)$$

where V is a potential in the living body and P is a three-dimensional impressed current vector. The expression (1) is the Poisson's equation. The potential V is determined by solving the expression (1) with an impressed current being supposed at each pixel position. In the expression (1), $\nabla$ is a symbol for differentiation. Next, the distribution of return current vectors R corresponding to the position of the impressed current is determined from $$R = -S\nabla \cdot V. \quad (2)$$

Further, a return current component is determined utilizing a linear relationship satisfied between the impressed current and the return current, and the determined return current component is removed from a total current.

As mentioned above, a return current must be removed in the case where an impressed current distribution in a living body is reconstructed from a magnetic field distribution measured in the exterior of the living body. However, the Kullmann's method involves a problem that an error is included since conductivity is considered as uniform and a problem that a large amount of computation time is required since the Poisson's equation is solved a number of times which is equal to the number of pixels multiplied by 3. Therefore, the practicability also comes into question.

SUMMARY OF THE INVENTION

An object of the present invention is to solve the above problems in the prior art, thereby providing a magnetic field generation source measuring method and system which can reproduce an actual form with a high fidelity and can determine an impressed current distribution corresponding to the distribution of electromotive forces in an object at a high processing speed with no need of a large amount of computation time.

To that end, a magnetic field generation source measuring method and system of the present invention for determining a magnetic field generation source in an object to be examined from a magnetic field measured at the exterior of the object, is characterized in that the object is represented by a model in which the object is divided into a plurality of cells (or fundamental cubic lattice units as shown in FIG. 1), and the resistance values of each cell in $\underline{x}$, $\underline{y}$ and $\underline{z}$ directions are calculated from information concerning the electric conductivity of the interior of the object beforehand measured by X-ray CT, MRI (magnetic resonance imaging) or the like. A total return current generated in accordance with the distribution of electromotive forces in the object is determined by use of estimated values of the intensities of a current source P in the $\underline{x}$, $\underline{y}$ and $\underline{z}$ directions and the resistance values with the electromotive force distribution in the object being supposed as the current source P. A vector of the sum of a current of the current source and the return current is determined for all of the cell. The second power of the absolute value of a difference between the determined vector of the sum and a current vector determined from the magnetic field in the interior of the object measured at the exterior of the object is subjected to summation for all of the cells. The estimated values of the current source intensities, which minimize the summation, are determined as the optimal estimated values of an electromotive force distribution in the object.

According to another feature of the present invention, the resistance value of each cell is represented by the form of an admittance (Y shown in FIG. 2), and an inverse matrix of an admittance matrix introduced from the Kirchhoff's law satisfied at a joint of each cell is determined (see expression (13) which will be shown later on). The inverse matrix is multiplied by a vector consisting of the electromotive force distribution to determine a potential at the joint of each cell (expression (5) which will be shown later on). A return current vector at each cell is determined from the value of the potential and the admittance of each cell.

According to a further feature of the present invention, the determination of the optimal estimated values of the electromotive force distribution in the object is made by slightly changing the estimated values of the current source intensities (see step 504 in FIG. 5) to calculate a difference between the above summation before the change and the above summation after the change (see step 505 in FIG. 5), substituting the estimated values of the current source intensities by those thereof after the change (see step 507 in FIG. 5) if the calculated difference is negative (see step 506 in FIG. 5), and repeating the substitution plural times.

In the present invention, in the case where a current distribution in an object to be examined is determined from a magnetic field distribution measured at the exterior of the object, a return current (or distributed current) subsidiarily generated is removed to determine the distribution of impressed currents in which electromotive forces are directly reflected. First, a total current distribution in the object including the return current is determined from the magnetic field distribution measured at the exterior of the object. Next, substituting the interior of the object by a three-dimensional cubic lattice network defined by dividing the interior of the object into N pixels and regarding each side of the pixel as a one-dimensional line, an admittance matrix of an area, for which the current distribution is to be estimated, is determined from the electric conductivity of the pixel. Representing an impressed current by a current source inserted in parallel with the one-dimensional line and supposing an estimated value of an impressed current distribution, the potential of each joint is determined from an inverse matrix of the admittance matrix. A return current distribution is determined from the determined potential and the admittance of each pixel. The impressed current distribution, which minimizes a square error between the total current distribution determined from the magnetic field and the sum of the supposed impressed current and the determined return current, is taken as an optimal estimated value.

Namely, the method according to the present invention includes calculating a vector of the sum of a current of a current source and a return current for all cells, as taught by an invention disclosed by the specification and drawings of Japanese Patent Application No. (Hei)3-202720 (U.S. Ser. No. 07/928782, filed on Aug. 13, 1992, now U.S. Pat. No. 5,243,984), subjecting the second power of the absolute of a difference between the vector of the sum and a current vector determined from a magnetic field to summation for all of the cells, and determining as an optimal estimated value of an electromotive force distribution an estimated value which minimizes the summation.

With the above construction, it becomes possible to determine the distribution of impressed currents which corresponds to the distribution of electromotive forces in the interior of an object to be examined.

DESCRIPTION OF THE PREFERRED EMBODIMENTS

The principle and embodiments of the present invention will now be explained in detail by use of the accompanying drawings.

Figure 1:
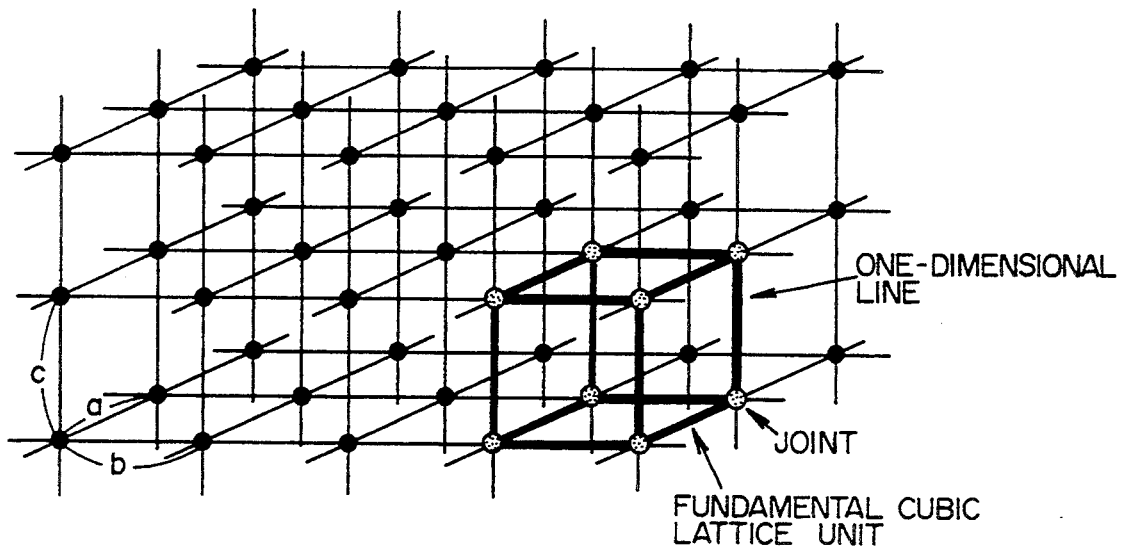
FIG. 1 is a perspective view of a three-dimensional cubic lattice network for explaining the principle of the present invention.
Figure 2:
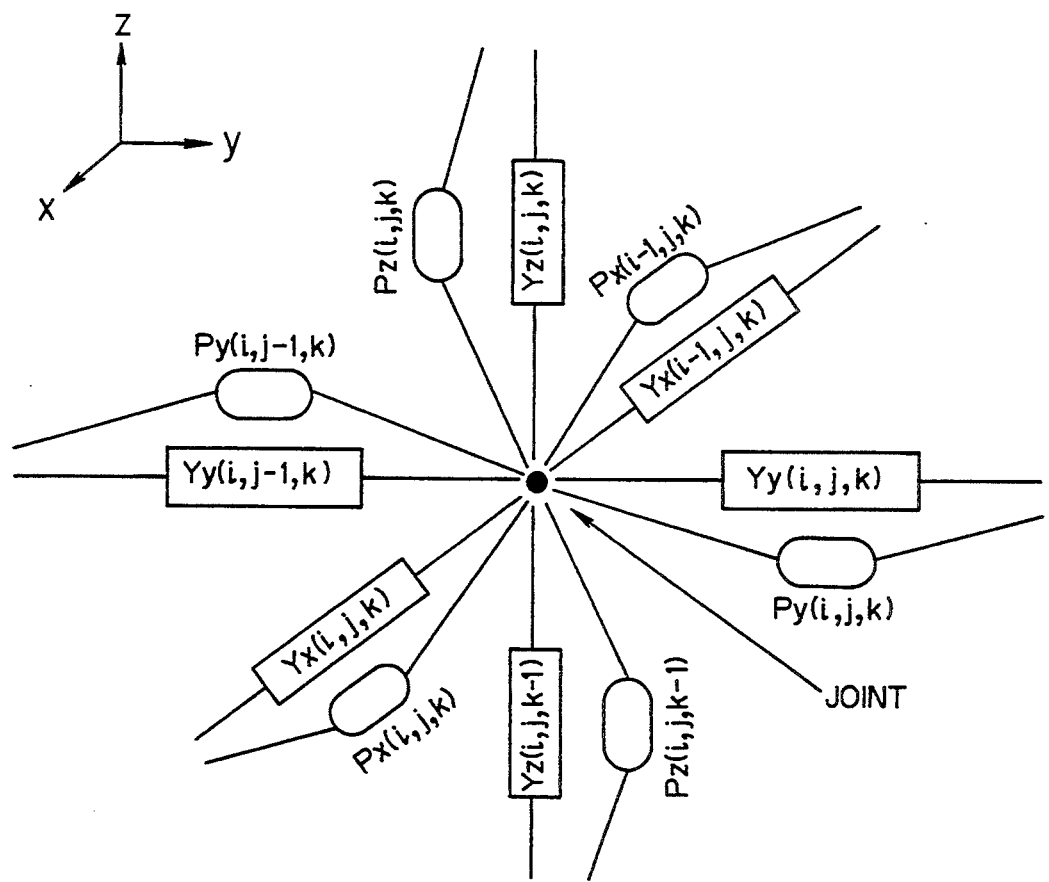
FIG. 2 is a diagram for explaining admittances and current sources connected to a joint shown in FIG. 1.

FIG. 1 is a perspective view of a three-dimensional cubic lattice network for explaining the principle of the present invention, and FIG. 2 is a diagram for explaining admittances and current sources connected to a joint shown in FIG. 1.

In the present invention, the interior of an object to be examined is substituted by a three-dimensional cubic lattice network which is defined by dividing the interior of the object into N pixels adapted to an actual external form and regarding each side of the pixel as a one-dimensional line, as shown in FIG. 1.

A section enclosed by thick solid lines in FIG. 1 represents a pixel. In FIG. 1 is shown a fundamental cubic lattice unit formed by one-dimensional lines which are defined by the lengths a, b and c of three sides of the pixel. The symbol of circle represents a joint or nodal point and the position of each joint is represented by (i,j,k) coordinate discretized by (x,y,z) coordinate.

Now assume that one-dimensional lines in positive $\underline{x}$, $\underline{y}$ and $\underline{z}$ directions from the joint (i,j,k) have admittances $Yx(i,j,\underline{k})$, $Yy(i,j,k)$ and $Yz(i,j,k)$, respectively, as shown in FIG. 2. Since the lengths of sides of a pixel formed by the one-dimensional lines in the positive $\underline{x}$, $\underline{y}$ and $\underline{z}$ directions from the joint (i,j,k) are a, b and c in the $\underline{x}$, $\underline{y}$ and $\underline{z}$ directions, as shown in FIG. 1, the admittances are calculated from the following expression:

$$\left. \begin{array}{l} Yx(i,j,k) = bcS(i,j,k)/a \\ Yy(i,j,k) = acS(i,j,k)/b \\ Yz(i,j,k) = baS(i,j,k)/c \end{array} \right\} \quad (3)$$

where S(i,j,k) is the electric conductivity of the pixel.

In the present invention, in the case where an impressed current exists, the current is represented by a current source inserted in parallel with the one-dimensional line. Namely, in the case where impressed currents Px(i,j,k), Py(i,j,k) and Pz(i,j,k) exist at the joint position of (i,j,k) in the $\underline{x}$, $\underline{y}$ and $\underline{z}$ directions, it is supposed that current sources having the amplitudes of Px(i,j,k), Py(i,j,k) and Pz(i,j,k) exist in parallel with the one-dimensional lines in the positive $\underline{x}$, $\underline{y}$ and $\underline{z}$ directions, as shown in FIG. 2. Provided that a potential at the joint (i,j,k) is V(i,j,k), the Kirchhoff's law gives the following expression:

$$\begin{array}{l} V(i,j,k)\{Yx(i,j,k) + Yy(i,j,k) + Yz(i,j,k) + \\ Yx(i - 1,j,k) + Yy(i,j - 1,k) + Yz(i,j,k - 1)\} - \\ V(i + 1,j,k)Yx(i,j,k) - V(i,j + 1,k)Yy(k,j,k) - \\ V(i,j,k + 1)Yz(i,j,k) - V(i - 1,j,k)Yx(i - 1,j,k) - \\ V(i,j - 1,k)Yy(i,j - 1,k) - V(i,j,k - 1)Yz(i,j,k - 1) = \\ P(i,j,k) \end{array} \quad (4)$$

where P(i,j,k) of the right side represents the sum of current sources flowing into the joint (i,j,k). Namely, P(i,j,k) is represented by the following equation:

$$\begin{array}{l} P(i,j,k) = Px(i - 1,j,k) - Px(i,j,k) + \\ Py(i,j - 1,k) - Py(i,j,k) + Pz(i,j,k - 1) - \\ Pz(i,j,k). \end{array} \quad (5)$$

Though the equation (4) holds for all joints, one of those equations is a linear dependency. For example, $N-1$ simultaneous equations hold with $V(1,1,1)$ being taken as a reference potential 0.

In the present invention, the potential $V(i,j,k)$ of each joint is first determined from the expressions (4) and (5) with $Px(i,j,k)$, $Py(i,j,k)$ and $Pz(i,j,k)$ being supposed as estimated values of an impressed current distribution. Distributed currents $Rx(i,j,k)$, $Ry(i,j,k)$ and $Rz(i,j,k)$, which are return currents at one-dimensional lines of each pixel, are determined from the determined potential $V(i,j,k)$ and admittances. Then, a calculation based on the following expression (6) is made using total currents $Qx(i,j,k)$, $Qy(i,j,k)$ and $Qz(i,j,k)$ determined from the measured value of a magnetic field:

$$E = \sum_i \sum_j \sum_k \{[Qx(i,j,k) - Rx(i,j,k) - Px(i,j,k)]^2 + [Qy(i,j,k) - Ry(i,j,k) - Py(i,j,k)]^2 + [Qz(i,j,k) - Rz(i,j,k) - Pz(i,j,k)]^2\}. \quad (6)$$

The values of $Px(i,j,k)$, $Py(i,j,k)$ and $Pz(i,j,k)$ minimizing E of the expression (6) are taken or determined as optimal estimated values.

In order to determine total currents $Qx(i,j,k)$, $Qy(i,j,k)$ and $Qz(i,j,k)$ in the object from the magnetic field distribution, one can use the above-mentioned Kullmann's method or other methods which include, for example, a method disclosed on pp. 603–606 of "Advances in Biomagnetism", edited by S. J. Williamson et al and published by Plenum Press, New York, a method disclosed by IEEE Transactions on Biomedical, ME-34 (1987), pp. 713–723, and a method disclosed by Applied Optics, Vol. 29 (1990), pp. 658–667.

Figure 3:
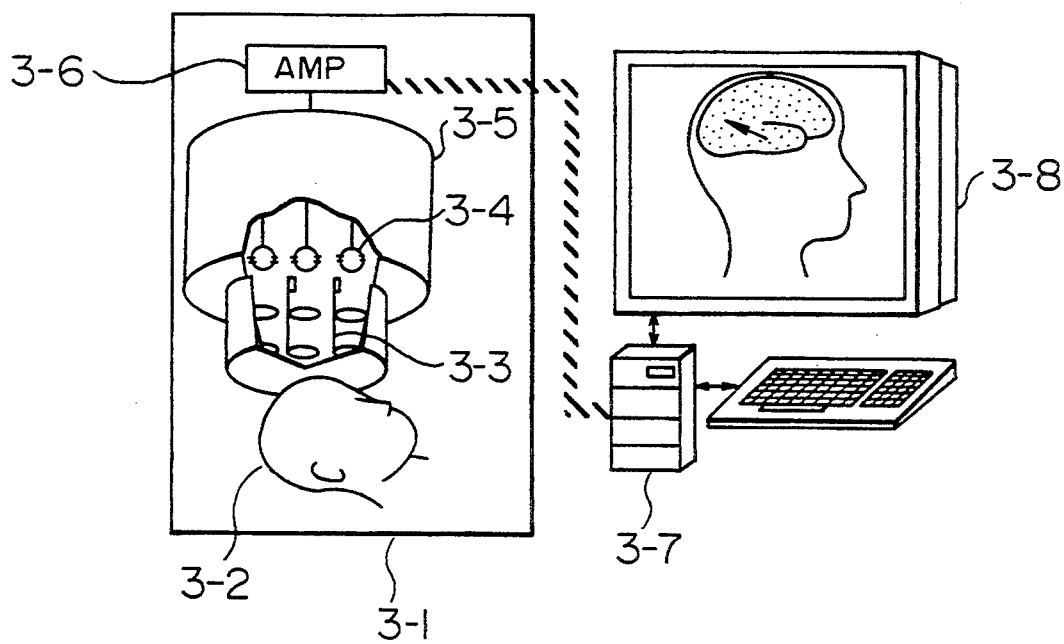
FIG. 3 is a diagram showing the construction of a biomagnetic imaging system according to an embodiment of the present invention.

FIG. 3 is a diagram showing the construction of a biomagnetism measuring system according to an embodiment of the present invention. In FIG. 3, reference numeral 3-1 denotes a magnetically shielded room, numeral 3-2 a patient or object to be examined, numeral 3-3 a detecting coil, numeral 3-4 a SQUID (superconducting quantum interference device), numeral 3-5 a helium Dewar vessel, numeral 3-6 a measuring circuit, numeral 3-7 a computer, and numeral 3-8 a display device.

After the object 3-2 to be examined has been placed into the magnetically shielded room 3-1, a magnetic field distribution on the surface of the object is measured. A signal from the detecting coil 3-3 is converted by the SQUID 3-4 into a voltage which is in turn amplified by the measuring circuit 3-6 and is thereafter sent to the computer 3-7. An impressed current distribution for a magnetic field source is estimated from the measurement signal by the computer 3-7 and is then displayed on the display device 3-8 in a form superimposed on a magnetic resonance image or an X-ray image.

Figure 4:
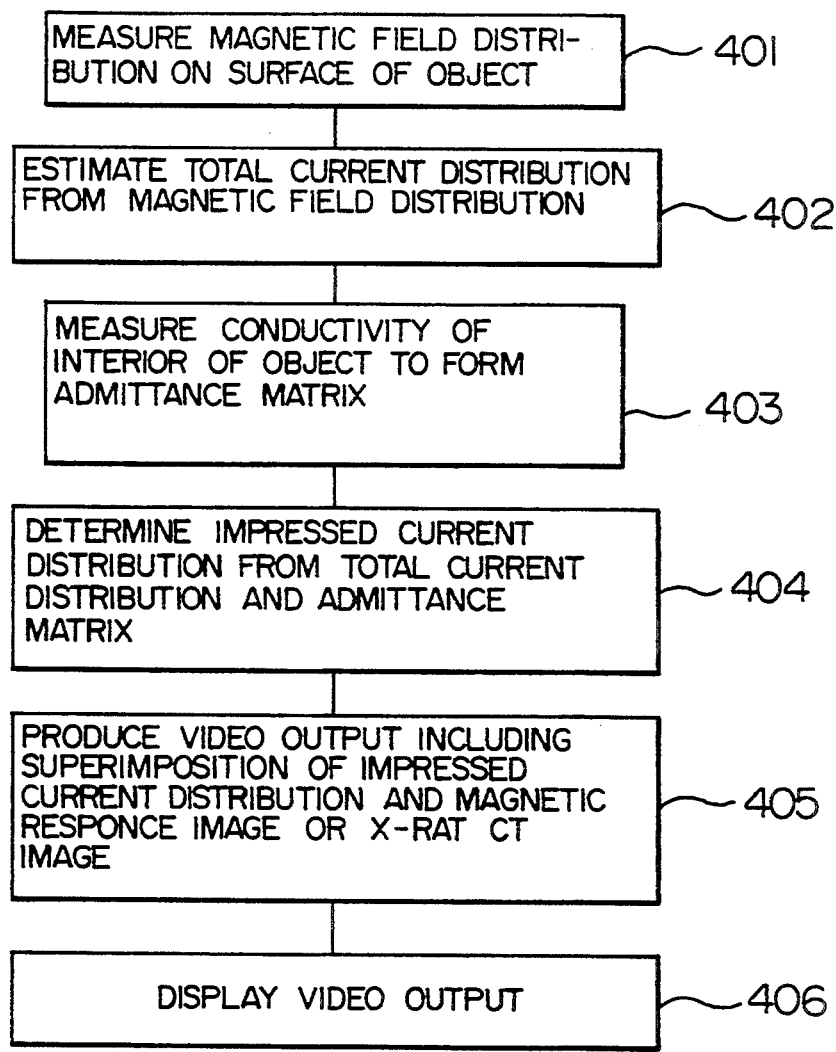
FIG. 4 is a flow chart showing a procedure for estimation of an impressed current distribution in the present invention.

FIG. 4 is a flow chart showing the operation of the measuring system shown in FIG. 3. First, a magnetic field distribution on the object surface is measured by a fluxmeter (step 401) and data obtained by the measurement is stored into a memory. A total current distribution is estimated using the measurement data (step 402). Next, an admittance matrix is calculated from the expressions (4) and (5) by use of an electric conductivity distribution in the object preliminarily measured using X-ray CT or MRI (step 403). An impressed current distribution is determined from the admittance matrix and the total current distribution in accordance with the teaching of the present invention (step 404). The impressed current distribution obtained is superimposed on a magnetic resonance image or X-ray CT image to produce a superimposed video output (step 405) which is in turn displayed on the display device (step 406).

As mentioned above, several methods have been proposed in order to determine the total current distribution from the magnetic field distribution measured. For example, in the Kullmann's method, the total current distribution is determined as follows. First, B is determined which represents a vector having as the m-th component a normal component B(m) of a magnetic field observed at the m-th measuring point on the surface of the object. Also, an area, for which the current distribution is to be reconstructed, is divided into pixels and the pixels are properly numbered. Representing the result of estimation of the current distribution by a vector Q, $Q(3(n-1)+1)$, $Q(3(n-1)+2)$ and $Q(3(n-1)+3)$ are allotted to the components of a current vector of the n-th pixel in the $\underline{x}$, $\underline{y}$ and $\underline{z}$ directions, respectively. At this time, a system matrix $\bar{H}$ representing a relationship between the vector B and the vector Q forms an $M \times (3N)$ matrix and is represented by the following expression (7) using a $1 \times 3$ matrix D:

$$H = \begin{bmatrix} D(1,1) & D(1,2) & \cdots & D(1,N) \\ D(2,1) & D(2,2) & & \\ \vdots & & \ddots & \vdots \\ D(M,1) & & \cdots & D(M,N) \end{bmatrix}. \quad (7)$$

In the present level of technique, only the normal component of the magnetic field is detected in a usual case. In the following, the explanation of the present embodiment will be continued taking such a case as an example. However, it is of course that the present invention is not limited to such an example and is applicable to the case where three components of the magnetic field are measured.

The matrix D(n, m) is represented by the following expression:

$$D(n,m) = \frac{1}{|rn - rm|^3 |nm|} \begin{pmatrix} ym \cdot zn - yn \cdot zm \\ xm \cdot zn - xn \cdot zm \\ ym \cdot xn - yn \cdot xm \end{pmatrix} \quad (8)$$

where $rn = (xn, yn, zn)$ is a position vector of the n-th pixel and $rm = (xm, ym, zm)$ is a position vector of the m-th measuring point.

In the Kullmann's proposal, the estimated value Q of the current distribution is determined from the following relational expression:

$$Q = [H^T H + gU]^{-1} H^T B \quad (9)$$

where g is a constant properly determined and U is a unit matrix. A superior symbol "−1" represents an inverse matrix, and a superior symbol "T" represents the transposition of a matrix. In the field of image processing, the expression (9) is known as the solution of minimum norm. The solution of minimum norm is disclosed by, for example, H. C. Andrews and B. R. Hunt, "Digital Image Restoration" Prentice Hall, Inc. Enslewood Cliffes, N.J. (1977), pp. 149.

Next, an admittance in one-dimensional line of each pixel is calculated from an electric conductivity distribution $S(i,j,k)$ in the object by use of the expression (3). In order to determine the electric conductivity distribution in the object, a three-dimensional image such as an X-ray CT image or magnetic resonance image is first obtained to acquire information concerning a three-dimensional distribution of tissues of the object in an area to be subjected to measurement. Further, if there are available tissues which have a little time lapse after extraction thereof from a living body, it is possible to know the electric conductivity of each tissue by measuring the electric resistance of that tissue. A three-dimensional distribution of electric conductivities in the area of the object to be subjected to measurement can be known from the electric conductivity of each tissue and the three-dimensional distribution of tissues in the object area acquired from the three-dimensional image such as an X-ray CT image or magnetic resonance image.

Next, a distribution of impressed currents is determined from the estimated current density value Q in accordance with the teaching of the present invention, as follows. First, joints $(i,j,k)$ excepting one selected as a reference potential are numbered in accordance with the numbering for pixels as mentioned above, to determine a solution space vector V which has a potential at the n-th joint as the n-th element. Further, an integral space vector P having $P(i,j,k)$ at the n-th joint as the n-th component is determined for $P(i,j,k)$ defined by the expression (5). As a result, the following expression (10) using an admittance matrix A is satisfied between the vectors V and P:

$$AV = P \tag{10}$$

The admittance matrix A is defined as follows:

$$A = \begin{bmatrix} a(1,1) & \cdots & a(1,N-1) \\ \cdot & & \cdot \\ \cdot & & \cdot \\ \cdot & & \cdot \\ a(N-1,1) & \cdots & a(N-1,N-1) \end{bmatrix} \tag{11}$$

Provided that the joints $(i,j,k)$, $(i-1,j,k)$, $(i,j-1,k)$, $(i,j,k-1)$, $(i+1,j,k)$, $(i,j+1,k)$ and $(i,j,k+1)$ are numbered by p, q, r, s, t, u and v, respectively, the following expression (12) is obtained from the expression (4):

$$\begin{aligned} a(p,p) &= Yx(i,j,k) + Yy(i,j,k) + Yz(i,j,k) + \\ & \quad Yx(i-1,j,k) + Yy(i,j,k) + Yz(i,j,k) \\ a(p,q) &= -Yx(i-1,j,k) \quad a(p,t) = -Yx(i,j,k) \\ a(p,r) &= -Yy(i,j-1,k) \quad a(p,u) = -Yy(i,j,k) \\ a(p,s) &= -Yz(i,j,k-1) \quad a(p,v) = -Yz(i,j,k) \end{aligned} \tag{12}$$

where $a(m,n)$ represents an $(m,n)$ element of the admittance matrix.

Accordingly, the solution space vector V is determined from the following expression:

$$V = [Ai]P \tag{13}$$

where [Ai] is an inverse matrix of A.

Accordingly, in order to determine an impressed current distribution from the total current distribution determined from the magnetic field distribution, the potential $V(i,j,k)$ of each joint is first determined from the expression (13) with estimated values $Px(i,j,k)$, $Py(i,j,k)$ and $Pz(i,j,k)$ of the impressed current distribution being supposed. And, distributed currents (or return currents) $Rx(i,j,k)$, $Ry(i,j,k)$ and $Rz(i,j,k)$ in one-dimensional lines of each pixel are determined from the following expression:

$$\begin{aligned} Rx(i,j,k) &= Yx(i,j,k)[V(i+1,j,k) - V(i,j,k)] \\ Ry(i,j,k) &= Yy(i,j,k)[V(i,j+1,k) - V(i,j,k)] \\ Rz(i,j,k) &= Yz(i,j,k)[V(i,j,k+1) - V(i,j,k)] \end{aligned} \tag{14}$$

Using total currents $Qx(i,j,k)$, $Qy(i,j,k)$ and $Qz(i,j,k)$ determined from the magnetic field, a calculation is made on the basis of the following expression:

$$E = \sum_i \sum_j \sum_k \{[Qx(i,j,k) - Rx(i,j,k) - Px(i,j,k)]^2 + \\ [Qy(i,j,k) - Ry(i,j,k) - Py(i,j,k)]^2 + \\ [Qz(i,j,k) - Rz(i,j,k) - Pz(i,j,k)]^2\}. \tag{15}$$

Then, the values of $Px(i,j,k)$, $Py(i,j,k)$ and $Pz(i,j,k)$, which minimize the cost function E of the expression (15), are determined as optimal estimated values.

An expression other than the expression (15) can be used as the cost function E. For example, provided that $CB(m)$ is a normal component of the magnetic field at the m-th measuring point on the object surface determined from a calculation using $Px(i,j,k)$, $Py(i,j,k)$, $Pz(i,j,k)$, $Rx(i,j,k)$, $Ry(i,j,k)$ and $Rz(i,j,k)$, the values of $Px(i,j,k)$, $Py(i,j,k)$ and $Pz(i,j,k)$ minimizing $$E = \sum_n [CB(m) - B(m)]^2 \tag{16}$$

are determined as optimal estimated values. The normal component $CB(m)$ can readily be determined by the Biot-Savart's equation of the electromagnetics from the position of each joint, the position of each measuring point and the direction and amplitude of a current flowing in the joint. As compared with the estimation of $Px(i,j,k)$, $Py(i,j,k)$ and $Pz(i,j,k)$ based on the cost function (15), the estimation of $Px(i,j,k)$, $Py(i,j,k)$ and $Pz(i,j,k)$ based on the cost function (16) is advantageous in that it gets off the influence of an error in estimating $Qx(i,j,k)$, $Qy(i,j,k)$ and $Qz(i,j,k)$.

Figure 5:
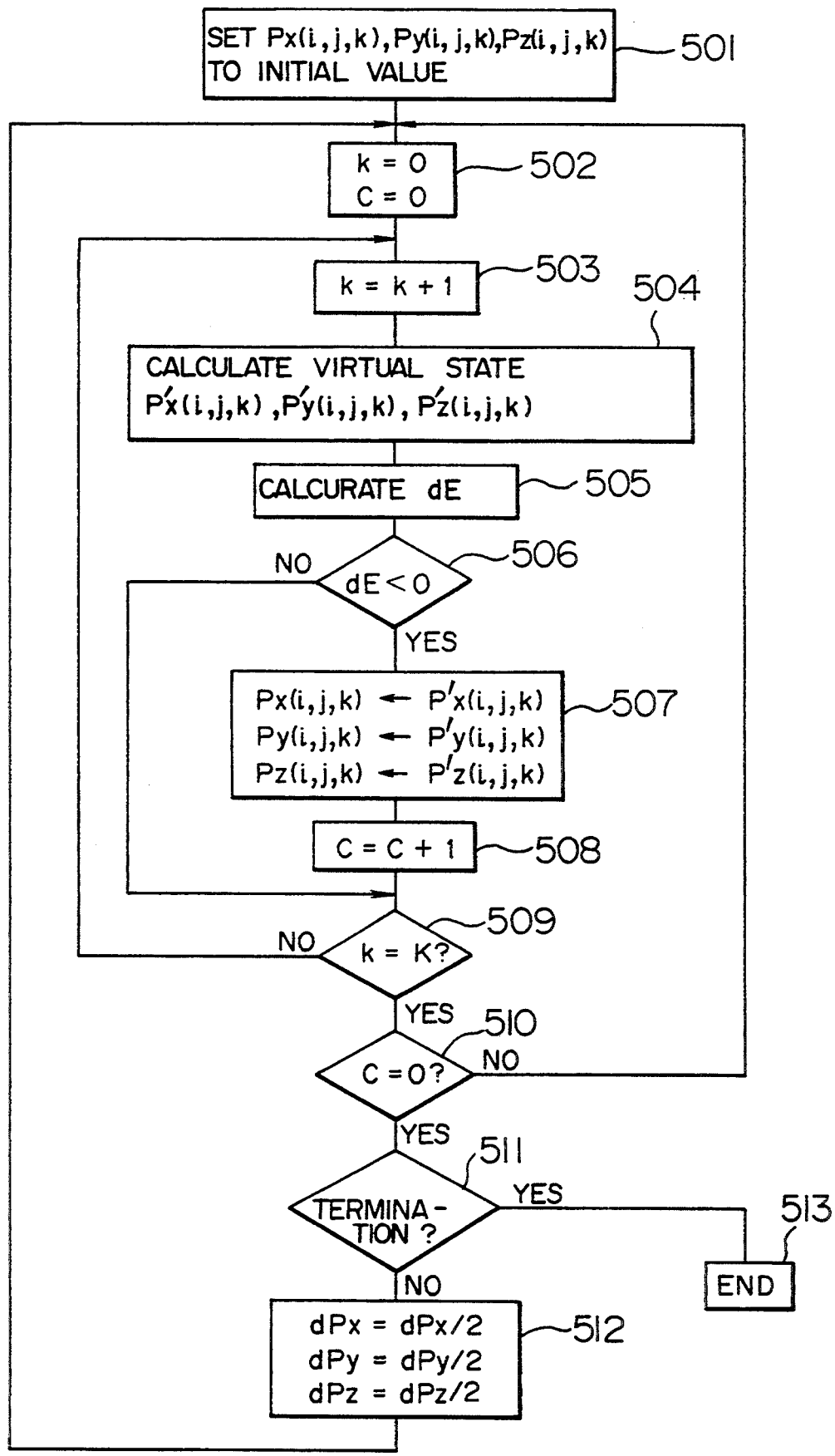
FIG. 5 is a flow chart showing an example of a calculation for optimization in embodying the present invention.

FIG. 5 is a flow chart showing a procedure for the problem of minimization in the present invention.

First, proper initial values are substituted for or set to $Px(i,j,k)$, $Py(i,j,k)$ and $Pz(i,j,k)$ (step 501) to determine the function E in accordance with the expression (6). Next, small displacements $dPx$, $dPy$ and $dPz$ are given to $Px(i,j,k)$, $Py(i,j,k)$ and $Pz(i,j,k)$ to provide $P'x(i,j,k)$, $P'y(i,j,k)$ and $P'z(i,j,k)$ (step 504). The function E is calculated for those new or trial values to determine a difference $dE$ from the previous value of E (step 505). If $dE$ is negative (step 506), the updating to the virtual or trial values $P'x(i,j,k)$, $P'y(i,j,k)$ and $P'z(i,j,k)$ as new estimated values is made (step 507) since the virtual values $P'x(i,j,k)$, $P'y(i,j,k)$ and $P'z(i,j,k)$ gets nearer to optimal values. Namely, the virtual values $P'x(i,j,k)$, P'y(i,j,k) and P'z(i,j,k) are substituted for the estimated values Px(i,j,k), Py(i,j,k) and Pz(i,j,k). If dE is positive (step 506), the updating of estimated values is not made since the virtual values P'x(i,j,k), P'y(i,j,k) and P'z(i,j,k) goes farther from optimal values. Namely, the estimated values Px(i,j,k), Py(i,j,k) and Pz(i,j,k) are left as they are.

The above procedure is repeated plural times. When a number of estimated values attendant upon the updating becomes zero after the trial is made certain times, the same procedure is repeated again with the magnitudes of displacements being decreased.

In FIG. 5, k is a counter for counting the number of times of trial and C is a counter for the number of times of updating of estimated values. In the shown example, the examination is made of whether or not C becomes zero with K times of trial (steps 509 and 510). It is preferable that the value of K is about 100 to 400.

The small displacements dPx, dPy and dPz may be generated using Gaussian random numbers each time the trial is made. In this case, when the number of estimated values to be updated become zero even if the trial is made certain times (step 510), the same procedure is repeated again (steps 502 and 503) while decreasing the magnitudes of Gaussian standard deviations by which the magnitudes of displacements are determined (step 512).

The ultimate termination of algorithm can be made when a limit imposed on the number of times of decrease of the magnitudes of displacements is reached.

Methods other than the above-mentioned optimization method may be used in order to determine the impressed current distribution which gives the minimum value of the function shown by the expression (15). There can be used a method which includes predicting a direction in which the function becomes the minimum in a solution space of the steepest descent method, conjugate gradation method or quasi-Newton method used in various fields, and changing estimated values in that direction. These methods are preferable in view of the efficiency of calculation. These methods are disclosed by, for example, H. Konno and H. Yamashita, "Non-Linear Programming" Nikkagiren (1978).

There may be the case where the procedure shown in FIG. 5 does not reach the optimal solution due to a small unevenness of the cost function attendant upon the discretization of a continuous quantity. In such a case, a technique called a simulated annealing method can be applied to the small change in the above-mentioned procedure. More particularly, even when dE is positive in step 506 of the above optimization method, the estimated values are updated at a certain probability instead of making no updating of the estimated values. This probability is initially selected to be very close to 1 and is thereafter gradually decreased in accordance with the degree of progression of calculation. The simulated annealing method is disclosed by, for example, E. Arts and J. Korst, "Simulated Annealing and Boltzmann Machine", John Wiley and Sons (1990).

A simpler method, though approximation is involved, can be considered as a method of determining the impressed current distribution from the total current distribution. Namely, the solution space vector V is determined by successively calculating a potential at each joint from the total current distribution Qx(i,j,k), Qy(i,j,k), Qz(i,j,k) in accordance with the following expression:

$$V(i+1,j,k) - V(i,j,k) = Qx(i,j,k)/Yx(i,j,k) \\ V(i,j+1,k) - V(i,j,k) = Qy(i,j,k)/Yy(i,j,k) \\ V(i,j,k+1) - V(i,j,k) = Qz(i,j,k)/Yz(i,j,k).$$ (16)

The determined vector V is multiplied by the admittance matrix A to determine the solution space vector P. The impressed current distribution can be determined from the element P(i,j,k) of the solution space vector P in accordance with the following approximate expression:

$$Px(i,j,k) \approx [P(i+1,j,k) - P(i,j,k)]/2 \\ Py(i,j,k) \approx [P(i,j+1,k) - P(i,j,k)]/2 \\ Pz(i,j,k) \approx [P(i,j,k+1) - P(i,j,k)]/2.$$ (17)

According to the present invention explained above in conjunction with the embodiment thereof, an impressed current distribution corresponding to the distribution of electromotive forces in an object to be examined can be determined in the case where a current distribution in the object is to be estimated from a magnetic field distribution on a surface of the object. Especially, in the case where the object is a living body, the present invention is very effective since the activity of the living body can directly be imaged.

We claim:

1. A magnetic field generation source measuring method of determining a magnetic field generation source in an object to be examined from a magnetic field generated in the interior of the object measured at the exterior of the object, comprising the steps of:

representing said object by a model in which said object is divided into a plurality of cells;

determining the resistance values of each of said cells in x, y, and z directions from information concerning the electric conductivity of the interior of said object beforehand measured;

determining a return current generated in accordance with the distribution of electromotive forces in said object by use of estimated values of the intensities of a current source in the x, y, and z directions and said resistance values with the electromotive force distribution in said object being supposed as said current source;

determining a vector of the sum of a current of said current source and the return current for all of said cells;

summing the second power of the absolute value of a difference between said vector of the sum and a current vector determined from the magnetic field in the interior of said object measured at the exterior of said object for all of said cells to obtain a sum value; and determining as an electromotive force distribution in said object the estimated values of the current source intensities which minimize said sum value.

2. A magnetic field generation source measuring method according to claim 1, wherein the resistance value of each of said cells is represented by the form of an admittance, an inverse matrix of an admittance matrix introduced from Kirchhoff's law satisfied at a joint of each cell is determined, said inverse matrix is multiplied by a solution space vector showing the electromotive force distribution to determine a potential at the joint of each cell, and a return current vector at each cell is determined from the value of said potential and the admittance of each cell.

3. A magnetic field generation source measuring method according to claim 2, wherein the determination of the electromotive force distribution in said object is made by slightly changing the estimated values of the current source intensities to calculate a difference between said sum value before the change and said sum value after the change, substituting the estimated values of the current source intensities by those thereof after the change if the calculated difference is negative, and repeating the substitution plural times.

4. A magnetic field generation source measuring method of determining a magnetic field generation source in an object to be examined from a magnetic field in the interior of the object measured at the exterior of the object, comprising the steps of:

representing said object by a model in which said object is divided into a plurality of cells;

determining the resistance values of each of said cells in x, y, and z directions from information concerning the electric conductivity of the interior of said object beforehand measured;

determining a return current generated in accordance with the distribution of electromotive forces in said object by use of estimated values of the intensities of a current source in the x, y, and z directions and said resistance values with the electromotive force distribution in said object being supposed as said current source;

summing the second power of the absolute value of a difference between a magnetic field at a magnetic field measuring point on an exterior of said object which is determined from a calculation from a vector of the sum of a current of said current source and said return current and the value of a magnetic field which is actually measured at said measuring point for all measuring points to obtain a sum value; and determining as an electromotive force distribution in said object the estimated values of the current source intensities which minimize said sum value.

5. A magnetic field generation source measuring method according to claim 4, wherein the resistance value of each of said cells is represented by the form of an admittance, an inverse matrix of an admittance matrix introduced from Kirchhoff's law satisfied at a joint of each cell is determined, said inverse matrix is multiplied by a solution space vector showing the electromotive force distribution to determine a potential at the joint of each cell, and a return current vector at each measuring point is determined from the value of said potential and the admittance of each cell.

6. A magnetic field generation source measuring method according to claim 5, wherein the determination of the electromotive force distribution in said object is made by slightly changing the estimated values of the current source intensities to calculate a difference between said sum value before the change and said sum value after the change, substituting the estimated values of the current source intensities by those thereof after the change if the calculated difference is negative, and repeating the substitution plural times.

* * * * *